United States Patent [19]

Zappelli et al.

[11] 4,088,639
[45] May 9, 1978

[54] MACROMOLECULAR ADENINE NUCLEOTIDE DERIVATIVES

[75] Inventors: Piergiorgio Zappelli, Monterotondo; Luciano Re, Rome; Walter Marconi, San Donato Milanese, all of Italy

[73] Assignee: Snamprogetti, S.p.A., Milan, Italy

[21] Appl. No.: 586,354

[22] Filed: Jun. 12, 1975

[30] Foreign Application Priority Data

Jun. 12, 1974 Italy .............................. 23900

[51] Int. Cl.$^2$ ............................................. C07H 19/20
[52] U.S. Cl. .............................. 260/112.5 R; 195/52; 536/27; 536/28; 536/29
[58] Field of Search ................ 260/211.5 R, 112.5 R; 536/27, 28, 29

[56] References Cited

U.S. PATENT DOCUMENTS

| 3,707,536 | 12/1972 | Haid et al. ................ 260/211.5 R |
| 3,758,456 | 9/1973 | Bax et al. ................ 260/211.5 R |
| 3,852,268 | 12/1974 | Prasad et al. ............. 260/211.5 R |
| 3,853,846 | 12/1974 | Rousseau et al. .......... 260/211.5 R |

*Primary Examiner*—Johnnie R. Brown
*Attorney, Agent, or Firm*—Morgan, Finnegan, Pine, Foley & Lee

[57] ABSTRACT

A macromolecular adenine derivative containing at least one unity having the general formula:

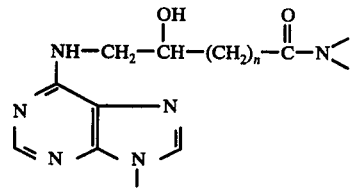

wherein, $n$ is 1, 2, 3 or 4; the radical:

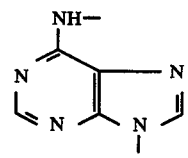

is derived from an adenine derivative wherein the amino group in position 6 in the adenine nucleus is functional; and the nitrogen atom, N<, belongs to a macromolecular compound containing one or more primary or secondary amine groups, is prepared by condensing the functional adenine derivative with a polymer containing one or more primary or secondary amine groups in the presence of a carbodiimide. These compounds are useful in affinity chromatographies or as unspreading co-enzymes.

3 Claims, No Drawings

MACROMOLECULAR ADENINE NUCLEOTIDE DERIVATIVES

The present invention relates to the preparation of macromolecular adenine derivatives and to the products obtained thereby containing one or more unities having the general formula

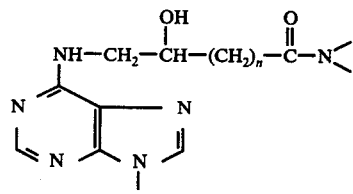

in which $n$ is 1, 2, 3, 4, wherein the radical

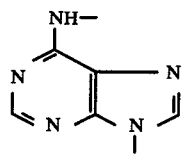

may be derived from any compound having an adenine nucleus such as, for instance, nicotinamide-adenine-dinucleotide, nicotinamide-adenine-dinucleotide phosphate, adenosine-monophosphate, cyclic adenosine-monophosphate, adenosine-diphosphate, adenosine-triphosphate, adenosine, ademine; and the nitrogen atom bound to a CO group belongs to a high molecular weight compound, either water soluble or insoluble, containing one or more primary or secondary amine groups (e.g., polylisine, ω-amino alkyl-polyacrylamides, polysaccharide esters of ω-amino alkyl carbamic acids, polyvinylamine, ω-amino alkyl esters or ω-amino alkyl-amides of polyglutamic acid, glass amino alkyl-silicium containing microspheres, polyethyleneimine, etc.)

It is known, from Italian patent application No. 22105 A/74 of Apr. 30, 1974 and the corresponding U.S. patent application, Ser. No. 572,653, filed Apr. 29, 1975, now U.S. Pat. No. 4,008,363 and owned by the assignee of this application, that there is a process for the preparation of adenine derivatives made functional by reacting a compound containing an adenine nucleus with carboxylic acids or ester epoxides. The reaction goes on until the amine group in 6 position of the adenine nucleus is made functional to give compounds having the general formula

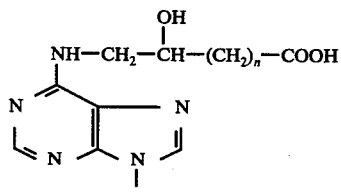

in which $n$ has one of the aforesaid values.

It has now been found, which is the subject of the present invention, that the aforesaid compounds made functional can react with a polymer containing at least a primary or secondary amine group, to give the above defined macromolecular adenine derivatives, in the presence of a carbodiimide, either water soluble [e.g., N-ethyl-N'-(3-dimethyl-aminopropyl) carbodiimide chlorohydrate] or insoluble (e.g., N, N'-dicyclohexyl-carbodiimide) as condensing agent.

The condensation reaction between the carboxylic group of the adenine derivative made functional and the amine group of the macromolecule to give the amide bonds is carried out in water or in a mixture formed by water and a water-soluble organic solvent (e.g., pyridine, tetrahydrofurane, dioxane, etc.) at temperatures of from +5° to +50° C, preferably at room temperature.

The macromolecular adenine derivatives, which are the subject of the invention, have several applications.

For instance in the case of the macromolecular nicotin-amide-adenine dinucleotide (NAD) derivatives, and the same thing may be applied also for the other macromolecular derivatives, they may be employed in affinity chromatographies or as unspreading co-enzymes.

Thus, when use is made of water-soluble macromolecules, they may be employed as water-soluble unspreading macromolecular co-enzymes. These broaden the field of application of the known enzymatic systems wherein the enzyme is physically englobed in insoluble structures, such as fibres, polyacrylamide gel, microcapsules, etc., which are macromolecule-proof.

In fact, when enzyme or polyenzymatic system are englobed together with a water-soluble macromolecular co-enzyme, both of them are in contact and, therefore, the co-enzyme is not dispersed outside the englobing structure, which was not possible heretofore because of the low molecular weight of the co-enzyme.

When use is made of insoluble macromolecules, the derivatives may be used for affinity chromatographies or enzymatic reactions to be carried out in the heterogeneous phase wherein the co-enzyme may be recovered.

EXAMPLE 1

Preparation of 4-(NAD-N$^6$)-3-hydroxybutyril-PEI (I, $n = 1$, N< is the radical of polyethyleneimine (PEI)

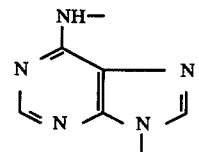

NAD radical)

To 127 mg of polyethyleneimine chlorohydrate at pH 6 (prepared by adding concentrated HCl to PEI having a molecular weight of about 50,000 and, then, by evaporating to dryness) in an aqueous solution at a concentration of 25% (weight/volume) were added 10 mg of nicotinamide 6-(2-hydroxy-3-carboxypropylamino) purine dinucleotide (II, $n = 1$

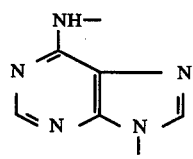

NAD radical)
dissolved in 0.125 ml of distilled water and then 10 mg of N,N'-dicyclohexylcarbodiimide dissolved in 0.125 ml of pyridine. The mixture was kept under stirring at room temperature for 36 hours and then filtered. The filtrate and the results of water-washings added thereto (total volume = 10 ml) were put in a centrifuge vessel and precipitated with 10 ml of 1 M phosphate buffer at pH 6. The whole was centrifuged for ten minutes at 39,000×g and the solution was separated from the polymeric precipitate through decantation. The polymer was further purified by dissolving it in 2 ml of a solution 2M as to NaCl and 0.05 M as to acetate buffer at pH 5.5; to the solution obtained thereby was added 8 ml of water and again precipitated with 10 ml of 1 M phosphate buffer at pH 6 and centrifugated for 10 minutes at 39,009×g, the polymer being recovered therefrom by decantation.

This purification procedure was repeated four times.

The product, again dissolved in a solution 2 M in NaCl and 0.05 M in acetate buffer at pH 5.5 was put in a dialysis test-tube and dialyzed for 24 hours against 250 ml of a solution 2 M in NaCl and $10^{-4}$ M in HCl. The same was then dialyzed against portions of 250 ml of $10^{-4}$ M HCl for four days, the solution being daily changed, and the product contained in the dialysis test-tube was recovered by a lyophilization. 90 mg of polymer were thus obtained, showing λ max at 266 ηµ.

The determination of NAD, active as co-enzyme, covalently bonded to the polymer was carried out in an aqueous solution of the polymer through a quantitative enzymatic reduction with alcohol-dehydrogenase from yeast in a 0.15 M Tris buffer at pH 9 in the presence of 0.5 M ethyl alcohol and 0.075 M semicarbazide chlorohydrate.

The spectrophotometric measurement of NADH carried out at 340 ηµ showed that 28.5µ moles of NAD, enzymatically reducible, were bonded per gram of polymer.

Macromolecular NAD thus obtained showed, with respect to natural NAD, a remarkable coenzyme activity rate in the presence of several dehydrogenases. For instance, in the presence of lactico-dehydrogenase from rabbit muscle, it showed a specific activity rate of 55% with respect to natural coenzyme. The determination was carried out in 0.1 M ammonium carbonate buffer at pH 8.5 and at 25° C.

EXAMPLE 2

Preparation of 4-(NAD-$N^6$)-3-hydroxybutyril-PEI (I, n-1, N< = polyethyleneimine (PEI) radical

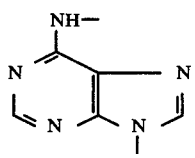

NAD radical)
To 125 mg of PEI obtained as described in example 1 at pH 6 in an aqueous solution at 25% (w/v) were added 40 mg of nicotinamide 6-(2-hydroxy-3-carboxypropylamino) purine-dinucleotide (II, $n = 1$

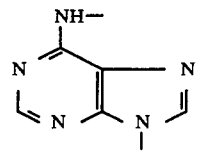

NAD radical)
dissolved in 0.5 ml of water and then 40 mg of N-ethyl-N'-(3-dimethylaminopropyl) carbodiimide chlorohydrate dissolved in 0.5 ml of water.

The pH of the mixture was brought to 5.5 by 1 M NaOH. The mixture was kept under stirring at room temperature for 48 hours.

After water had been added in order to reach a total volume of 10 ml the solution was set in a centrifuge vessel and precipitated with 10 ml of 1 M phosphate buffer at pH 6. The whole was centrifugated for 10 minutes at 39.000×g and the solution was separated from the polymeric precipitate. In order to further purify the polymer, it was dissolved in 2 ml of a solution 2 M as NaCl and 0.05 M as acetate buffer at pH 5.5; to the solution obtained thereby was added 8 ml of water and again precipitated with 10 ml of 1 M phosphate buffer at pH 6; then it was centrifugated for ten minutes at 39.000×g the polymer being recovered by decantation. This purification procedure was carried out four times. The product, again dissolved in a solution 2 M as to NaCl and 0.05 M as acetate buffer at pH 5.5, was put in a dialysis vessel and dialyzed for 24 hours against 250 ml of a solution 2 M as to NaCl and $10^{-4}$M as to HCl. Then it was dialyzed against portions of 250 ml of 10 M HCl for 4 days, the solution being daily changed, and the product contained in the dialysis vessel was recovered by lyophilization.

85.7 g of polymer were obtained having λ max at 266µ.

The determination of NAD, active as coenzyme, covalently bonded to the polymer was carried out in an aqueous solution of the polymer through a quantitative enzymatic reduction with alcohol-dehydrogenase from yeast in 0.15 M buffer Tris at pH 9 in the presence of 0.5 M ethyl alcohol and 0.075 M semicarbazine chlorohydrate. The spectrophotometric measurement at 340 mµ of formed NADH derivative indicated that 125µ moles of enzymatically reducible NAD were bonded per gram of polymer.

EXAMPLE 3

Preparation of 4-(NAD-$N^6$)-3-hydroxybutyril-PLYS (I, $n = 1$, N< = radical of poly-L-lysine (PLYS)

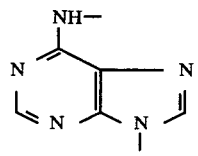

NAD radical,
To 100 mg of poly L-lysine bromohydrate, having ~ 50,000 molecular weight, dissolved in 1 ml of water were added 40 mg of nicotinamide 6-(2-hydroxy-3-carboxypropylamino) purine dinucleotide (II, $n = 1$

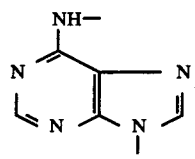

NAD radical)

dissolved in 0.5 ml of water and then 40 mg of N-ethyl-N'-(3-dimethylaminopropyl) carbodiimide chlorohydrate dissolved in 0.5 ml of water.

The pH of the mixture was brought to 5.5 with 1 M NaOH.

The reaction mixture was then kept under stirring at room temperature for 48 hours.

The mixture was then transferred to a dialysis vessel and dialyzed for 24 hours against 250 ml of a solution 2 M in NaCl and $10^{-4}$ M in HCl. It was then dialyzed against portions of 250 ml of $10^{-4}$ M HCl for four days, the solution being daily changed the product contained in the dyalisis vessel was recovered by lyophylization - 75.4 mg of polymer were obtained, $\lambda$ max at 266 m $\mu$.

The determination of NAD, active from a coenzyme point of view, covalently bonded to poly L-lysine was carried out through spectophotometry, after an enzymatic quantitative reduction of polymer with alcohol dehydrogenase from yeast in buffer Tris 0.15 M at pH 9 in the presence of 0.5 M ethyl alcohol and 0.075 M semicarbazide chlorohydrate, by reading 340 m$\mu$ of formed NAD derivative. Therefrom 90$\mu$moles of enzymatically reducible NAD were covalently bonded per gram of polymer.

EXAMPLE 4

Preparation of 4-(NAD-$N^6$)-3-hydroxybutryril-AHSEPH (I, $n = 1$, N< = radical of Sepharose 4B made functional, by means of the cyanogen bromide method, with 1.6 diaminohexane, containing from 6 to 10 moles of amine residues per gel ml (AHSEPH),

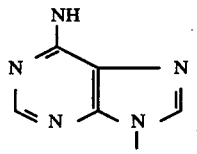

NAD radical)

500 mg of AHSEPH (trade name AH - Sepharose-4B) were foamed by 0.5 M NaCl solution, then washed by 200 ml of 0.5 M NaCl and then by distilled water. When the gel reached about a 2ml volume, there was added 92 mg of nicotinamide 6-(2-hydroxy-3-carboxypropylamino) purine dinucleotide (II, $n = 1$

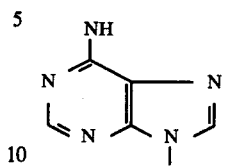

NAD radical)

dissolved in 2 ml of distilled water and the pH was brought to 5 with 1 M NaOH. The suspension was stirred at room temperature by means of a mechanical stirrer at low speed and then there was added, drop by drop, with 75 mg of N-ethyl-N'-(3-dimethylaminopropyl) carbodiimide chlorohydrate dissolved in 2 ml of distilled water. During the first 5 hours the pH had to be kept about 5 (M HCl was added) and a slow stirring was also maintained. The reaction was carried out for 24 hours and thereafter gel was filtered and washed, first with 200 ml of a solution IM in NaCl and $10^{-4}$ M in HCl and then with distilled water to give ~ 1.8 ml of moist gel, $\lambda$ max at 266 m$\mu$.

The NAD content covalently bonded to Sepharose gel was determined by spectrophotometry measurements at 266 m$\mu$ as to coenzyme in the oxidized form (NAD) and at 340 m$\mu$ as to coenzyme (NADH) enzymatically reduced by alcohol-dehydrogenase from yeast in buffer Tris 0.15 M at pH of 9 in the presence of 0.5 M ethyl alcohol and 0.075 M semicarbazide chlorohydrate.

The ultraviolet spectra were carried out by suspending gel in an aqueous solution at 1% of Polyox WSR 301 which decelerated the sedimentation of gel itself.

From the measurement of the optical density at 266 m$\mu$ it was shown that a total of 2.04$\mu$moles of NAD were covalently bonded per gram of dry Sepharose.

From the enzymatic reduction and optical density measurements at 340 m$\mu$ it was shown that the amount of enzymatically reducible NAD covalently bonded to polymer was 1.15$\mu$ moles per gram of dry Sepharose.

What we claim is:

1. 4-(6-nicotinamide adenine dinucleotide)-3-hydroxybutyril polyethyleneimine.

2. 4-(6-nicotinamide adenine dinucleotide)-3-hydroxybutyril poly-L-lysine.

3. 4-(6-nicotinamide adenine dinucleotide)-3-hydroxybutyril Sepharose 4B.

* * * * *